United States Patent [19]
Inoue

[11] Patent Number: 6,143,180
[45] Date of Patent: Nov. 7, 2000

[54] METHOD FOR SEPARATING OPTICAL ISOMERS

[75] Inventor: Keizo Inoue, Hyogo, Japan

[73] Assignee: Daicel Chemical Industries, Ltd., Osaka, Japan

[21] Appl. No.: 09/297,236

[22] PCT Filed: Oct. 16, 1998

[86] PCT No.: PCT/JP98/04696

§ 371 Date: Apr. 26, 1999

§ 102(e) Date: Apr. 26, 1999

[87] PCT Pub. No.: WO99/21811

PCT Pub. Date: May 6, 1999

[30] Foreign Application Priority Data

Oct. 23, 1997 [JP] Japan ................................... 9-290759
Aug. 24, 1998 [JP] Japan ................................. 10-236904

[51] Int. Cl.[7] .................................................. B01D 15/08
[52] U.S. Cl. ...................... 210/635; 210/656; 210/198.2; 210/502.1
[58] Field of Search .................................... 210/635, 656, 210/659, 198.2, 502.1; 536/123.1

[56] References Cited

U.S. PATENT DOCUMENTS

| | | | |
|---|---|---|---|
| 4,818,394 | 4/1989 | Okamoto et al. ..................... | 210/198.2 |
| 4,861,872 | 8/1989 | Okamoto et al. ..................... | 536/18.7 |
| 4,912,205 | 3/1990 | Okamoto et al. ..................... | 536/20 |
| 5,202,433 | 4/1993 | Okamoto et al. ..................... | 540/200 |
| 5,271,833 | 12/1993 | Funkenbusch ....................... | 210/198.2 |
| 5,734,043 | 3/1998 | Murakami et al. ................... | 536/30 |

FOREIGN PATENT DOCUMENTS

| | | | |
|---|---|---|---|
| 3-27326 | 2/1991 | Japan ................................ | 210/198.2 |
| 5-85947 | 4/1993 | Japan ................................ | 210/198.2 |
| 5-215736 | 8/1993 | Japan . | |
| 5-346423 | 12/1993 | Japan . | |
| 9-194399 | 7/1997 | Japan ................................ | 210/198.2 |

OTHER PUBLICATIONS

PTO Translation of Japan Patent No. 9–194399, Translation No. 2000–1531 Feb. 2000 pp. 1–22.

*Primary Examiner*—Ernest G. Therkorn
*Attorney, Agent, or Firm*—Flynn, Thiel, Boutell & Tanis, P.C.

[57] ABSTRACT

The present invention provides a method for separating optical isomers, which enables the optical resolution of compounds which could not sufficiently be resolved optically by the reversed-phase chromatographic methods of the prior art. The present invention further provides a method for separating optical isomers by liquid chromatography with a separating agent comprising a polysaccharide derivative as the active component, which comprises conducting the chromatographic separation under the reversed-phase conditions by using a basic mobile phase.

9 Claims, 13 Drawing Sheets

METHOD FOR SEPARATING OPTICAL ISOMERS

REFERENCE TO RELATED APPLICATIONS

This application is a 371 of PCT/JP98/04696 filed Oct. 16, 1998.

FIELD OF THE INVENTION

The present invention relates to a method for separating optical isomers by liquid chromatography with a separating agent comprising a polysaccharide derivative as the active ingredient.

DESCRIPTION OF THE PRIOR ART

As well known, optical isomers of a compound generally differ in the activities for the living body, though they are chemically the same. Accordingly, it is extremely important in the fields of drugs, agricultural chemicals and biochemistry-related industries to prepare an optically pure compound for the purpose of enhancing drug effects per unit dose and inhibiting side effects and drug-induced sufferings. Preferential crystallization, diastereomeric method, chromatography, enzymatic method, and separative membrane method have been known as means for the separation of isomeric mixtures, i.e., optical resolution. Among them, chromatography is generally widely employed, because efficient optical resolution can be attained by simple and easy operation.

The separating agent to be packed into a column used in chromatographic optical resolution includes optically active polymethacrylate esters, optically active polyacrylamides, optically active crown compounds, optically active amino acid derivatives and polysaccharide derivatives. In particular, a separating agent comprising a polysaccharide derivative is excellent in separating power and general-purpose properties and therefore is used in the optical resolution of many compounds. Several separating agents comprising polysaccharide derivatives respectively are disclosed in U.S. Pat. No. 4,818,394, U.S. Pat. No. 4,861,872, U.S. Pat. No. 4,912,205, U.S. Pat. No. 5,202,433, and so on.

The optical resolution with such a separating agent is conducted mainly under so-called normal-phase conditions wherein an organic solvent such as hexane/2-propanol mixture is used as the mobile phase. However, it is difficult to elute a highly polar compound under normal-phase conditions, while many highly polar compounds are used as drugs. Thus, optical resolution only by normal-phase chromatography is not satisfactory for all compounds. Under these circumstances, methods of optical resolution by reversed-phase chromatography have also been developed. For example, described are mixtures of water with ethanol in U.S. Pat. No. 4,818,394, mixtures of water-soluble organic solvents with acids in JP-A-5-346,423, mixtures of water-soluble organic solvents and buffers in JP-A-5-215, 736, mixtures of water-soluble with water in U.S. Pat. No. 5,734,043 and mixtures of water-soluble organic solvents with water or buffers containing various salts in JP-A-3-27, 326 as the mobile phase to be used in the reversed-phase chromatography. However, these mobile phases are neutral or acidic, and many compounds could not be optically resolved by the use of such a neutral or acidic mobile phase.

Accordingly, the problem that the present invention is to solve is to provide a method for separating optical isomers which permits optical resolution of compounds which could not sufficiently be optically resolved by the reversed-phase chromatographic methods of the prior art.

SUMMARY OF THE INVENTION

The inventors of the present invention have intensively studied and have found that the above problem can be solved by using a basic mobile phase under reversed-phase conditions. Namely, the present invention relates to a method for separating optical isomers by liquid chromatography with a separating agent comprising a polysaccharide derivative as the active ingredient, wherein the chromatographic separation is conducted under reversed-phase conditions by using a basic mobile phase.

In other words, the present invention is a method for separating optical isomers by liquid chromatography filled with a separating agent comprising a polysaccharide derivative as the active component in the reverse phase condition using a basic mobile phase.

The term "reversed-phase conditions" means using a mobile phase which contains water.

The polysaccharide to be used as the raw material for preparing the polysaccharide derivative according to the present invention may be any optically active one selected from among synthetic polysaccharides, natural polysaccharides and modified natural polysaccharides. In particular, it is preferable to use cellulose, amylose, β-1,4-chitosan, chitin, β-1,4-mannan, β-1,4-xylan, inulin, α-1,3-glucan or β-1,3-glucan, because such a polysaccharide can easily be prepared as a high-purity product. It is preferable that the polysaccharide have a number-average degree of polymerization (i.e., a mean number of pyranose or furanose rings contained per molecule) of 5 or above. Further, the upper limit thereof is preferably 500 or below from the standpoint of handleability, though it is not particularly restricted.

The polysaccharide derivative to be used in the present invention is one prepared by substituting part or all, preferably at least 85%, of the hydroxyl hydrogen atoms of the above polysaccharide, and includes esters, carbamates and ethers thereof. Among them, carbamates of polysaccharides are preferable, aromatic carbamates thereof being still preferable. Specific examples of the polysaccharide derivative to be favorably used in the present invention include amylose tris(3,5-dimethylphenylcarbamate), cellulose tris(3,5-dimethylphenylcarbamate) and cellulose tris(4-methylbenzoate).

The above polysaccharide derivative is used as the separating agent in a particle state or in a state supported on a carrier such as silica gel. The use thereof in a supported state is conventional.

The basic mobile phase to be used in the present invention is one prepared by adding a basic compound to a mixture comprising water and a water-soluble organic solvent. The preferable proportion of water and a water-soluble organic solvent is in the range of 90/10–40/60(v/v). The preferable additional amount of the basic compound is 10–100 mmol for water.

Preferable examples of the water-soluble organic solvent include acetonitrile, methanol, ethanol and 2-propanol, and those of the basic compound may include either of inorganic compounds and organic compounds. Specifically, basic inorganic salts such as phosphates, carbonates and borates; and hydroxides such as quaternary ammonium hydroxides, tertiary oxonium hydroxides, quaternary phosphonium hydroxides and secondary iodonium hydroxides. Among them, it is still preferable to use a basic phosphate such as $K_2HPO_4$ or $Na_3PO_4$ or a mixture thereof, and a basic borate such as $Na_2B_4O_7$ or a mixture thereof with $H_3BO_3$.

The present invention enables the optical resolution of compounds which could not sufficiently be resolved optically by the reversed-phase chromatographic methods of the prior art, which widens the variety of objects of optical resolution.

DESCRIPTION OF THE PREFERRED EMBODIMENTS

EXAMPLES

The present invention will now be described in detail by referring to the following Examples and Comparative Examples, though the present invention is not limited by them.

The parameters "k'" and "α" used in the Examples and Comparative Examples are defined as follows:

$$k' \text{ (capacity ratio)} = \frac{\text{retention time of a compound} - \text{dead time}}{\text{dead time}}$$

$$\alpha \text{ (seperation factor)} = \frac{k' \text{ of more strongly adsorbed compound}}{k' \text{ of more weakly adsorbed compound}}$$

Example 1

Figure 1:
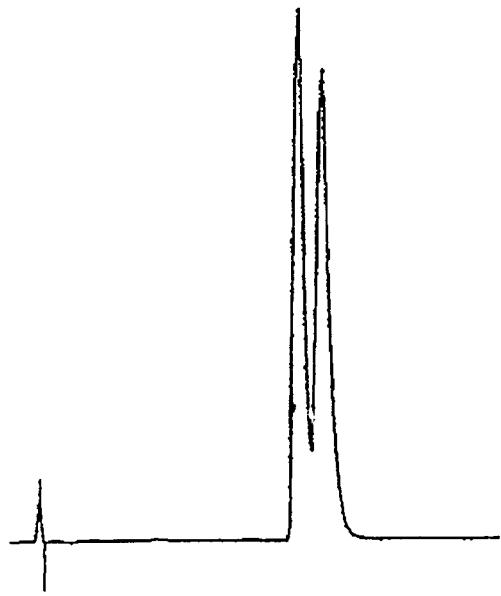
FIG. 1 is a column chromatogram of propranolol as obtained in Example 1.

The optical resolution of propranolol was conducted by using as the mobile phase a mixture comprising a 20 mM aqueous solution (pH 10) of $K_2HPO_4/Na_3PO_4$ and $CH_3CN$ at a volume ratio of 70:30. The column used was a stainless steel column having a length of 15 cm and an inner diameter of 0.46 cm and filled with a stationary phase comprising silica gel and amylose tris(3,5-dimethylphenylcarbamate) supported thereon. The flow rate of the mobile phase was 0.5 ml/min and the column temperature was 25° C. The eluted optical isomers were detected by the use of an ultraviolet detector at a wavelength of 254 nm. The chromatogram thus obtained is shown in FIG. 1, and the retention times and capacity ratios of both enantiomers and the separation factor are given in Table 1.

Comparative Example 1

Figure 2:
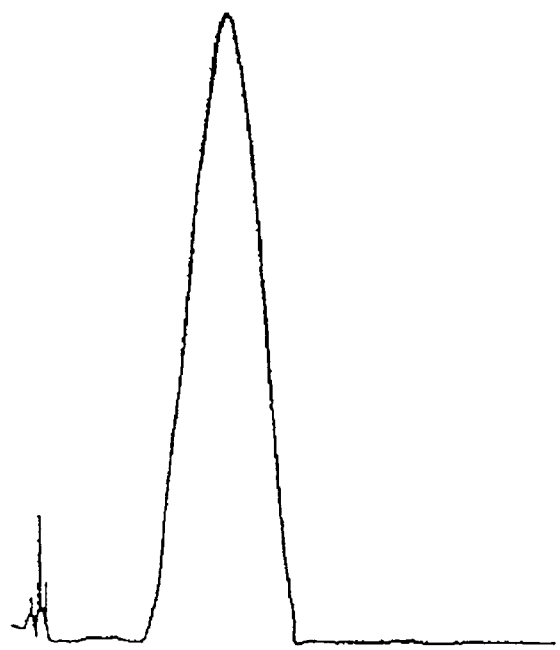
FIG. 2 is another column chromatogram of propranolol as obtained in Comparative Example 1.

The optical resolution of propranolol was conducted by using as the mobile phase a mixture comprising $H_2O$ and $CH_3CN$ at a volume ratio of 70:30. The other experimental conditions were the same as in Example 1. The chromatogram thus obtained is shown in FIG. 2, and the retention times and capacity ratios of both enantiomers and the separation factor are given in Table 1. The separation of propranolol into enantiomers failed.

Comparative Example 2

Figure 3:
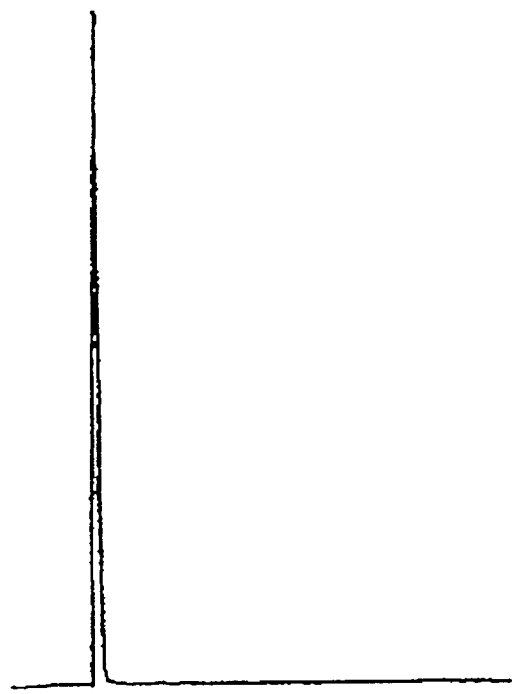
FIG. 3 is a further column chromatogram of propranolol as obtained in Comparative Example 2.

The optical resolution of propranolol was conducted by using as the mobile phase a mixture comprising a 0.5 M aqueous solution of $NaClO_4$ and $CH_3CN$ at a volume ratio of 70:30. The other experimental conditions were the same as in Example 1. The chromatogram thus obtained is shown in FIG. 3, and the retention times and capacity ratios of both enantiomers and the separation factor are given in Table 1. The separation of propranolol into enantiomers failed.

TABLE 1

| | Propranolol | | | | |
| --- | --- | --- | --- | --- | --- |
| | retention time (min.) | | capacity ratio (k') | | separation factor |
| | 1 | 2 | 1 | 2 | (α) |
| Ex. 1 | 37.7 | 40.73 | 9.56 | 10.41 | 1.09 |
| Comp. Ex. 1 | 25.05 | — | 6.02 | — | 1 |
| Comp. Ex. 2 | 8.83 | — | 1.47 | — | 1 |

Example 2

Figure 4:
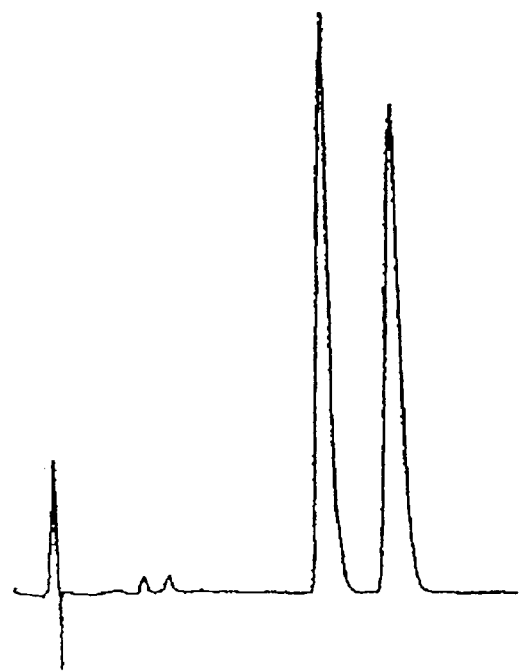
FIG. 4 is a column chromatogram of alprenolol as obtained in Example 2.

The optical resolution of alprenolol was conducted by using as the mobile phase a mixture comprising a 20 mM aqueous solution (pH 10) of $K_2HPO_4/Na_3PO_4$ and $CH_3CN$ at a volume ratio of 70:30. The other experimental conditions were the same as in Example 1. The chromatogram thus obtained is shown in FIG. 4, and the retention times and capacity ratios of both enantiomers and the separation factor are given in Table 2.

Comparative Example 3

Figure 5:
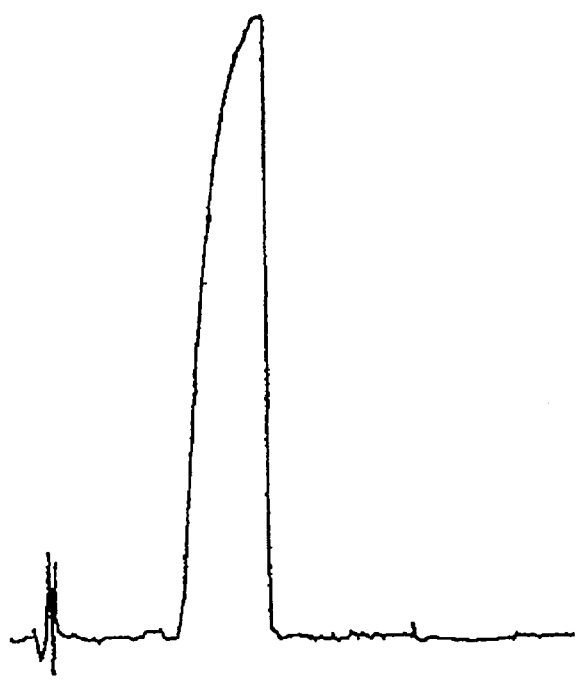
FIG. 5 is another column chromatogram of alprenolol as obtained in Comparative Example 3.

The optical resolution of alprenolol was conducted by using as the mobile phase a mixture comprising $H_2O$ and $CH_3CN$ at a volume ratio of 70:30. The other experimental conditions were the same as in Example 1. The chromatogram thus obtained is shown in FIG. 5, and the retention times and capacity ratios of both enantiomers and the separation factor are given in Table 2. The separation of alprenolol into enantiomers failed.

Comparative Example 4

Figure 6:
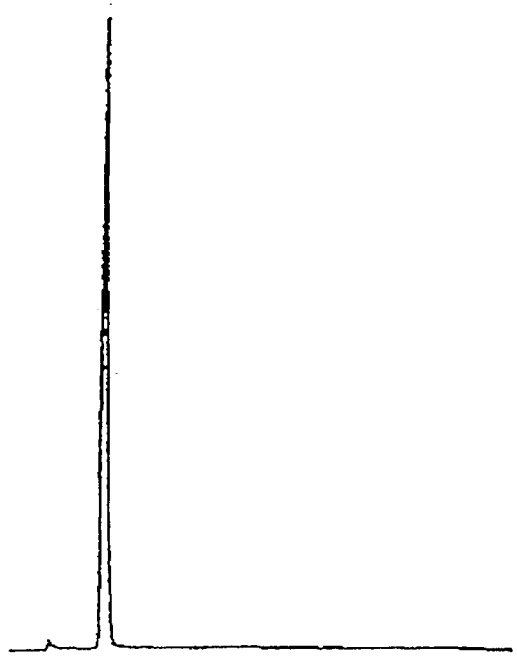
FIG. 6 is a further column chromatogram of alprenolol as obtained in Comparative Example 4.

The optical resolution of alprenolol was conducted by using as the mobile phase a mixture comprising a 0.5 M aqueous solution of $NaClO_4$ and $CH_3CN$ at a volume ratio of 70:30. The other experimental conditions were the same as in Example 1. The chromatogram thus obtained is shown in FIG. 6, and the retention times and capacity ratios of both enantiomers and the separation factor are given in Table 2. The separation of alprenolol into enantiomers failed.

TABLE 2

| | Alprenolol | | | | |
|---|---|---|---|---|---|
| | retention time (min.) | | capacity ratio (k') | | separation factor |
| | 1 | 2 | 1 | 2 | ($\alpha$) |
| Ex. 2 | 29.63 | 36.17 | 7.3 | 9.13 | 1.25 |
| Comp. Ex. 3 | 22.28 | — | 5.24 | — | 1 |
| Comp. Ex. 4 | 8.54 | — | 1.39 | — | 1 |

Example 3

Figure 7:
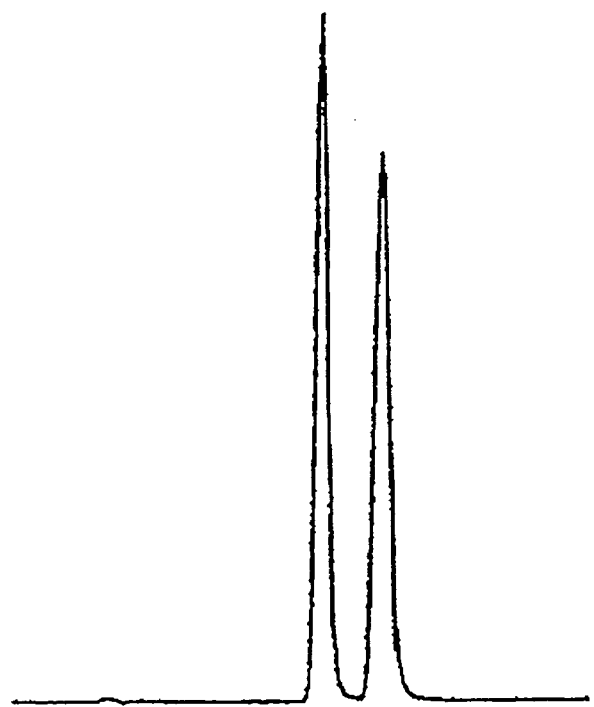
FIG. 7 is a column chromatogram of pindolol as obtained in Example 3.

The optical resolution of pindolol was conducted by using as the mobile phase a mixture comprising a 20 mM aqueous solution (pH 10) of $K_2HPO_4/Na_3PO_4$ and $CH_3CN$ at a volume ratio of 70:30. The other experimental conditions were the same as in Example 1. The chromatogram thus obtained is shown in FIG. 7, and the retention times and capacity ratios of both enantiomers and the separation factor are given in Table 3.

Comparative Example 5

Figure 8:
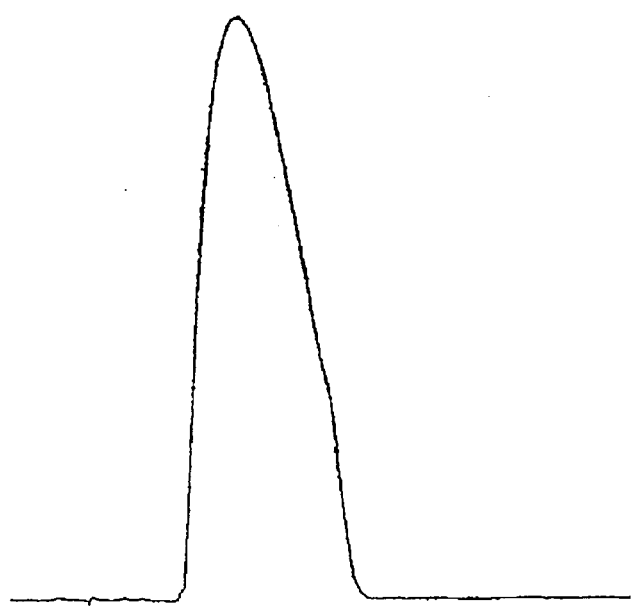
FIG. 8 is another column chromatogram of pindolol as obtained in Comparative Example 5.

The optical resolution of pindolol was conducted by using as the mobile phase a mixture comprising $H_2O$ and $CH_3CN$ at a volume ratio of 70:30. The other experimental conditions were the same as in Example 1. The chromatogram thus obtained is shown in FIG. 8, and the retention times and capacity ratios of both enantiomers and the separation factor are given in Table 3. The separation of pindolol into enantiomers failed.

Comparative Example 6

Figure 9:
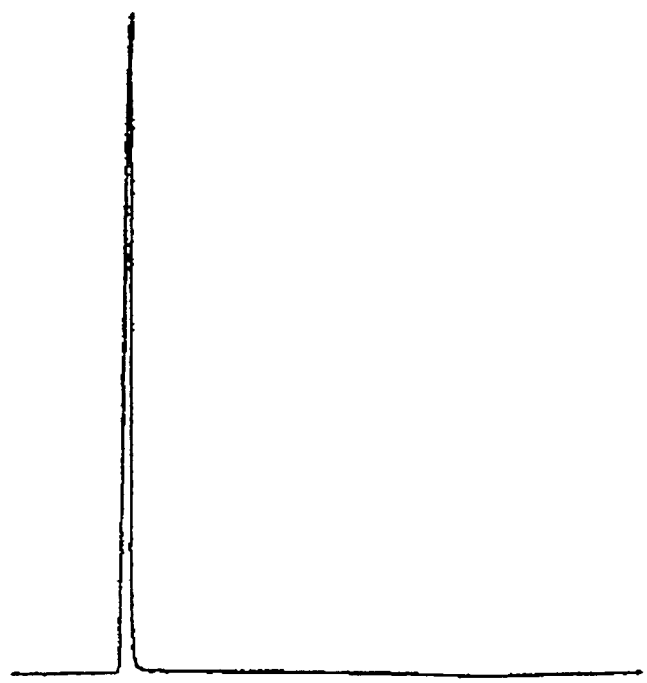
FIG. 9 is a further column chromatogram of pindolol as obtained in Comparative Example 6.

The optical resolution of pindolol was conducted by using as the mobile phase a mixture comprising a 0.5 M aqueous solution of $NaClO_4$ and $CH_3CN$ at a volume ratio of 70:30. The other experimental conditions were the same as in Example 1. The chromatogram thus obtained is shown in FIG. 9, and the retention times and capacity ratios of both enantiomers and the separation factor are given in Table 3. The separation of pindolol into enantiomers failed.

TABLE 3

| | Pindolol | | | | |
|---|---|---|---|---|---|
| | retention time (min.) | | capacity ratio (k') | | separation factor |
| | 1 | 2 | 1 | 2 | ($\alpha$) |
| Ex. 3 | 12.35 | 14.82 | 2.46 | 3.15 | 1.28 |
| Comp. Ex. 5 | 11.08 | — | 2.1 | — | 1 |
| Comp. Ex. 6 | 5.04 | — | 0.41 | — | 1 |

Example 4

Figure 10:
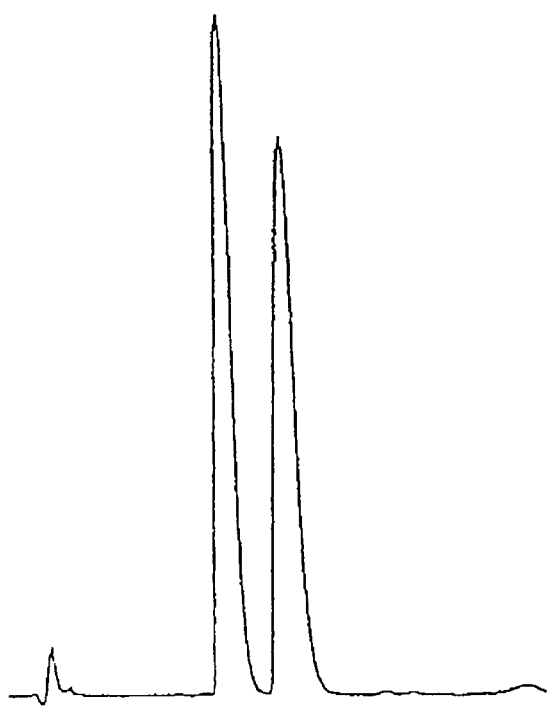
FIG. 10 is a column chromatogram of nefopam as obtained in Example 4.

The optical resolution of nefopam was conducted by using as the mobile phase a mixture comprising a 20 mM aqueous solution (pH 9) of $Na_2B_4O_7/H_3BO_3$ and $CH_3CN$ at a volume ratio of 60:40. The other experimental conditions were the same as in Example 1. The chromatogram thus obtained is shown in FIG. 10, and the retention times and capacity ratios of both enantiomers and the separation factor are given in Table 4.

Comparative Example 7

Figure 11:
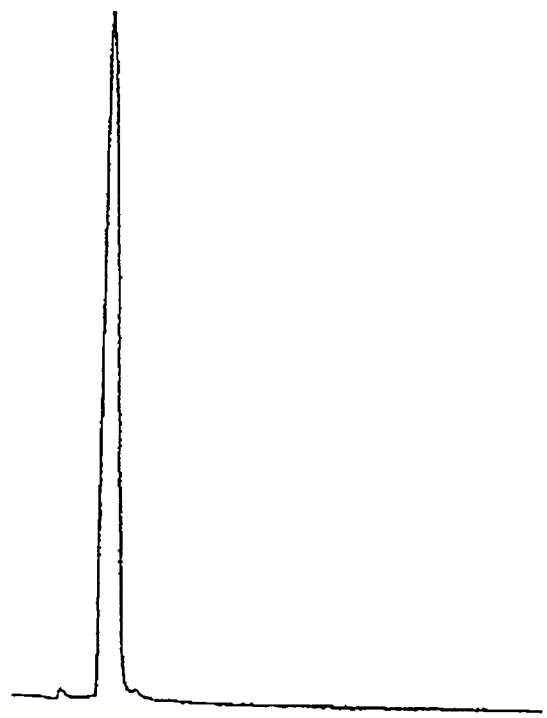
FIG. 11 is another column chromatogram of nefopam as obtained in Comparative Example 7.

The optical resolution of nefopam was conducted by using as the mobile phase a mixed solvent comprising a 0.1 M aqueous solution (pH 4.7) of $KPF_6$ and $CH_3CN$ at a volume ratio of 60:40. The other experimental conditions were the same as in Example 1. The chromatogram thus obtained is shown in FIG. 11, and the retention times and capacity ratios of both enantiomers and the separation factor are given in Table 4. The separation of nefopam into enantiomers failed.

TABLE 4

| | Nefopam | | | | |
|---|---|---|---|---|---|
| | retention time (min.) | | capacity ratio (k') | | separation factor |
| | 1 | 2 | 1 | 2 | ($\alpha$) |
| Ex. 4 | 16.30 | 20.78 | 3.53 | 4.77 | 1.35 |
| Comp. Ex. 7 | 7.49 | — | 1.08 | — | 1 |

Example 5

Figure 12:
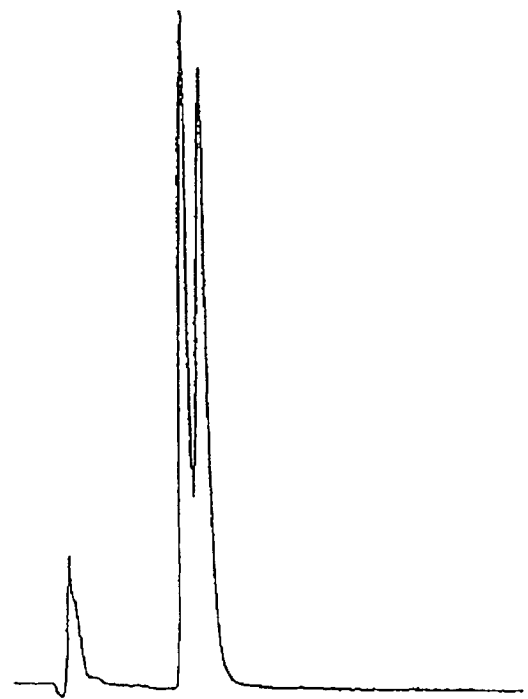
FIG. 12 is a column chromatogram of chlorprenaline as obtained in Example 5.

The optical resolution of chlorprenaline was conducted by using as the mobile phase a mixture comprising a 20 mM aqueous solution (pH 9) of $Na_2B_4O_7/H_3BO_3$ and $CH_3CN$ at a volume ratio of 60:40. The other experimental conditions were the same as in Example 1. The chromatogram thus obtained is shown in FIG. 12, and the retention times and capacity ratios of both enantiomers and the separation factor are given in Table 5.

Comparative Example 8

Figure 13:
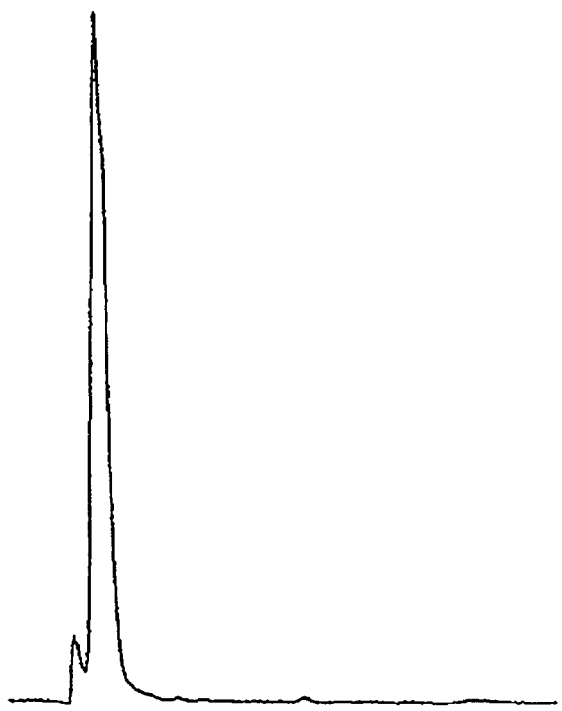
FIG. 13 is another column chromatogram of chlorprenaline as obtained in Comparative Example 8.

The optical resolution of chlorprenaline was conducted by using as the mobile phase a mixed solvent comprising a 0.1 M aqueous solution (pH 4.7) of $KPF_6$ and $CH_3CN$ at a volume ratio of 60:40. The other experimental conditions were the same as in Example 1. The chromatogram thus obtained is shown in FIG. 13, and the retention times and capacity ratios of both enantiomers and the separation factor are given in Table 5. The separation of chlorprenaline into enantiomers failed.

TABLE 5

Chlorprenaline

| | retention time (min.) | | capacity ratio (k') | | separation factor |
|---|---|---|---|---|---|
| | 1 | 2 | 1 | 2 | (α) |
| Ex. 5 | 10.22 | 11.25 | 1.84 | 2.13 | 1.16 |
| Comp. Ex. 8 | 5.16 | — | 0.43 | — | 1 |

Example 6

Figure 14:
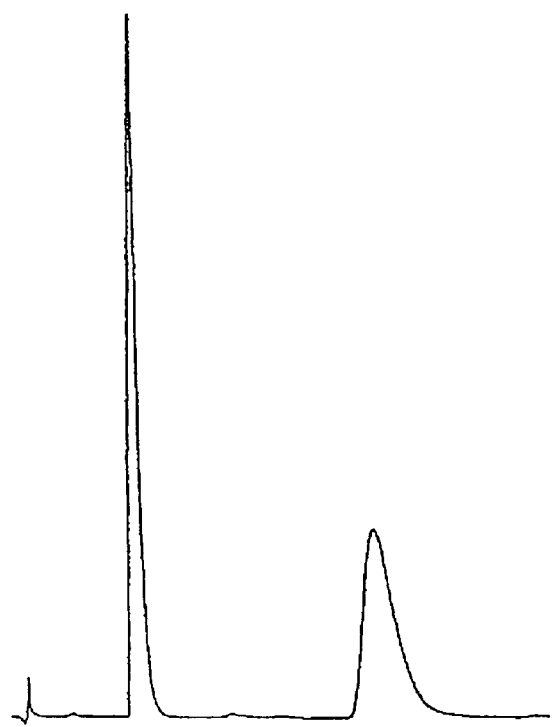
FIG. 14 is a column chromatogram of metixene as obtained in Example 6.

The optical resolution of metixene was conducted by using as the mobile phase a mixture comprising a 20 mM aqueous solution (pH 9) of $Na_2B_4O_7/H_3BO_3$ and $CH_3CN$ at a volume ratio of 40:60. The other experimental conditions were the same as in Example 1. The chromatogram thus obtained is shown in FIG. 14, and the retention times and capacity ratios of both enantiomers and the separation factor are given in Table 6.

Comparative Example 9

Figure 15:
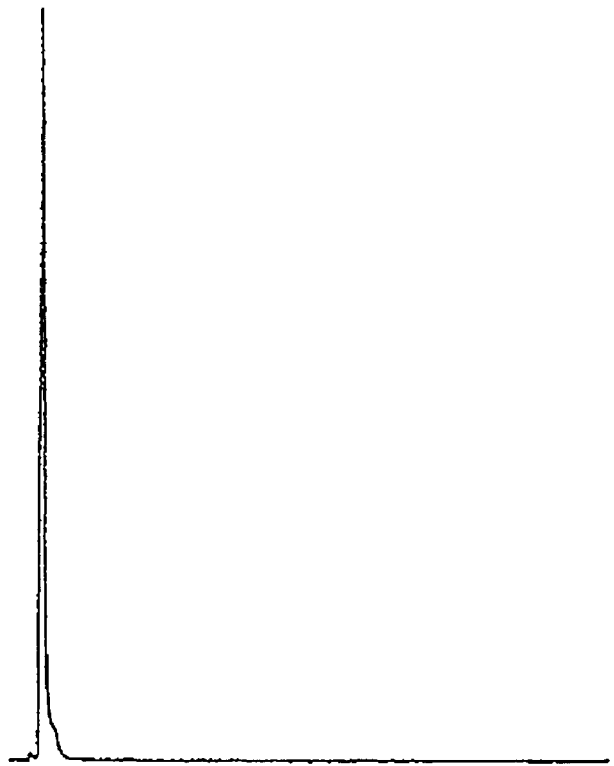
FIG. 15 is another column chromatogram of metixene as obtained in Comparative Example 9.

The optical resolution of metixene was conducted by using as the mobile phase a mixed solvent comprising a 0.1 M aqueous solution (pH 4.7) of $KPF_6$ and $CH_3CN$ at a volume ratio of 40:60. The other experimental conditions were the same as in Example 1. The chromatogram thus obtained is shown in FIG. 15, and the retention times and capacity ratios of both enantiomers and the separation factor are given in Table 6. The separation of metixene into enantiomers failed.

TABLE 6

Metixene

| | retention time (min.) | | capacity ratio (k') | | separation factor |
|---|---|---|---|---|---|
| | 1 | 2 | 1 | 2 | (α) |
| Ex. 6 | 21.11 | 60.54 | 4.86 | 15.82 | 3.26 |
| Comp. Ex. 9 | 5.33 | — | 0.48 | — | 1 |

Example 7

Figure 16:
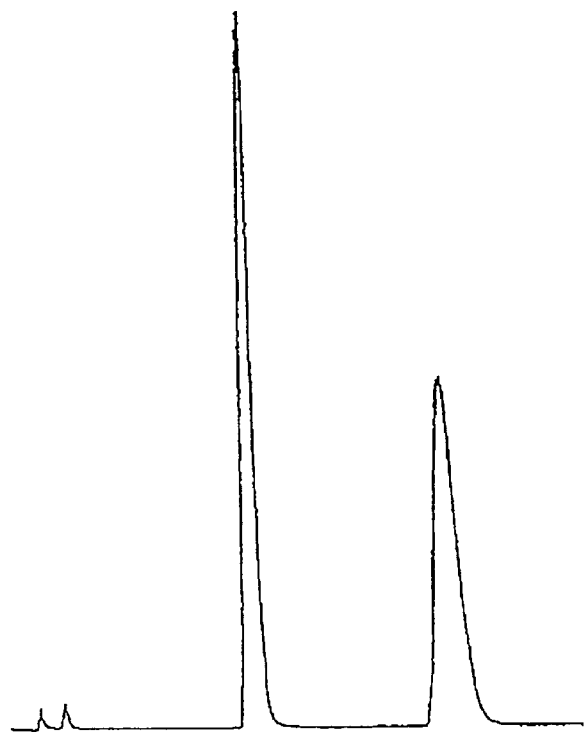
FIG. 16 is a column chromatogram of perisoxal as obtained in Example 7.

The optical resolution of perisoxal was conducted by using as the mobile phase a mixture comprising a 20 mM aqueous solution (pH 9) of $Na_2B_4O_7/H_3BO_3$ and $CH_3CN$ at a volume ratio of 40:60. The other experimental conditions were the same as in Example 1. The chromatogram thus obtained is shown in FIG. 16, and the retention times and capacity ratios of both enantiomers and the separation factor are given in Table 7.

Comparative Example 10

Figure 17:
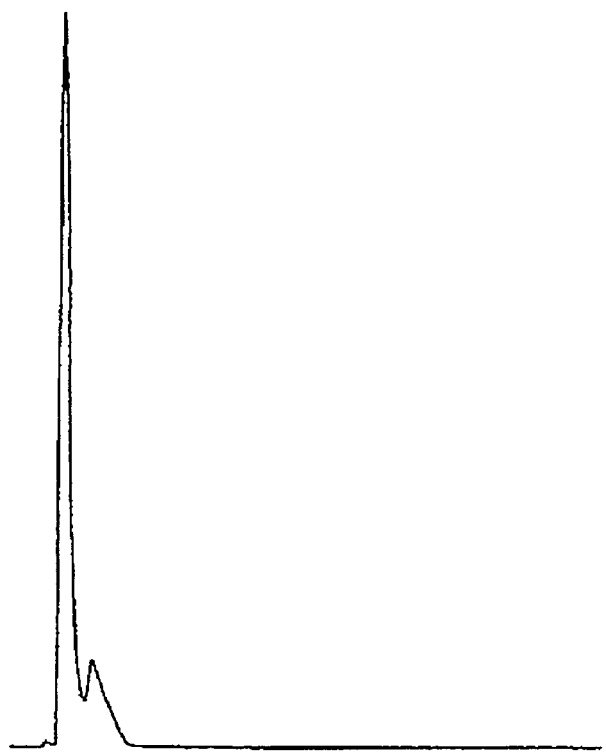
FIG. 17 is another column chromatogram of perisoxal as obtained in Comparative Example 10.

The optical resolution of perisoxal was conducted by using as the mobile phase a mixed solvent comprising a 0.1 M aqueous solution (pH 4.7) of $KPF_6$ and $CH_3CN$ at a volume ratio of 40:60. The other experimental conditions were the same as in Example 1. The chromatogram thus obtained is shown in FIG. 17, and the retention times and capacity ratios of both enantiomers and the separation factor are given in Table 7. The separation of perisoxal into enantiomers failed.

TABLE 7

Perisoxal

| | retention time (min.) | | capacity ratio (k') | | separation factor |
|---|---|---|---|---|---|
| | 1 | 2 | 1 | 2 | (α) |
| Ex. 7 | 25.22 | 45.42 | 6.00 | 11.62 | 1.94 |
| Comp. Ex. 10 | 5.47 | — | 0.52 | — | 1 |

Example 8

Figure 18:
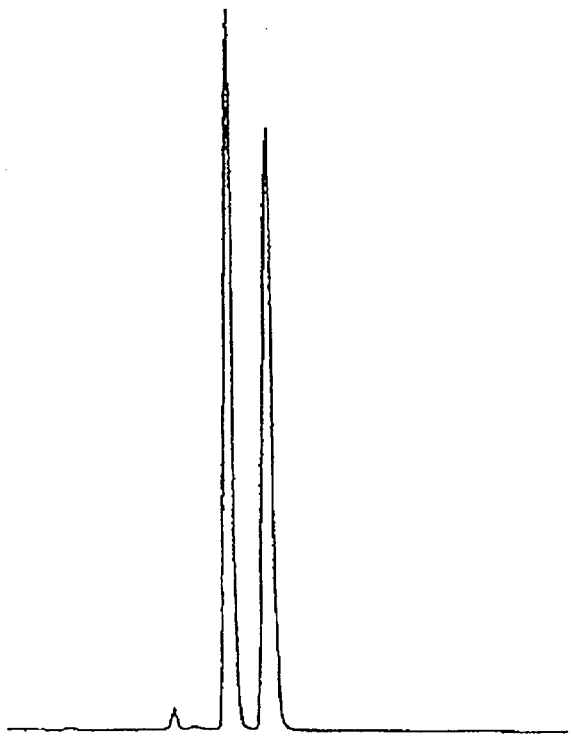
FIG. 18 is a column chromatogram of tolperisone as obtained in Example 8.

The optical resolution of tolperisone was conducted by using as the mobile phase a mixture comprising a 20 mM aqueous solution (pH 9) of $Na_2B_4O_7/H_3BO_3$ and $CH_3CN$ at a volume ratio of 40:60. The other experimental conditions were the same as in Example 1. The chromatogram thus obtained is shown in FIG. 18, and the retention times and capacity ratios of both enantiomers and the separation factor are given in Table 8.

Comparative Example 11

Figure 19:
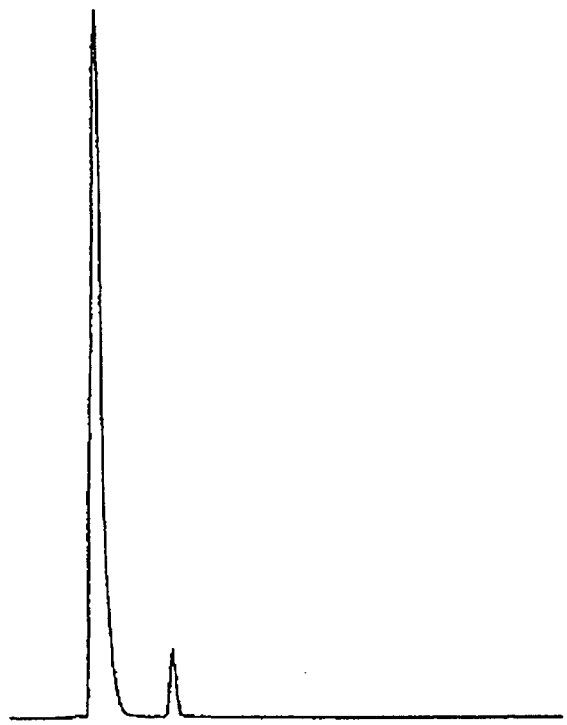
FIG. 19 is another column chromatogram of tolperisone as obtained in Comparative Example 11.

The optical resolution of tolperisone was conducted by using as the mobile phase a mixed solvent comprising a 0.1 M aqueous solution (pH 4.7) of $KPF_6$ and $CH_3CN$ at a volume ratio of 40:60. The other experimental conditions were the same as in Example 1. The chromatogram thus obtained is shown in FIG. 19, and the retention times and capacity ratios of both enantiomers and the separation factor are given in Table 8. The separation of tolperisone into enantiomers failed.

TABLE 8

Tolperisone

| | retention time (min.) | | capacity ratio (k') | | separation factor |
|---|---|---|---|---|---|
| | 1 | 2 | 1 | 2 | (α) |
| Ex. 8 | 11.78 | 13.82 | 2.27 | 2.84 | 1.25 |
| Comp. Ex. 11 | 4.79 | — | 0.33 | — | 1 |

Example 9

Figure 20:
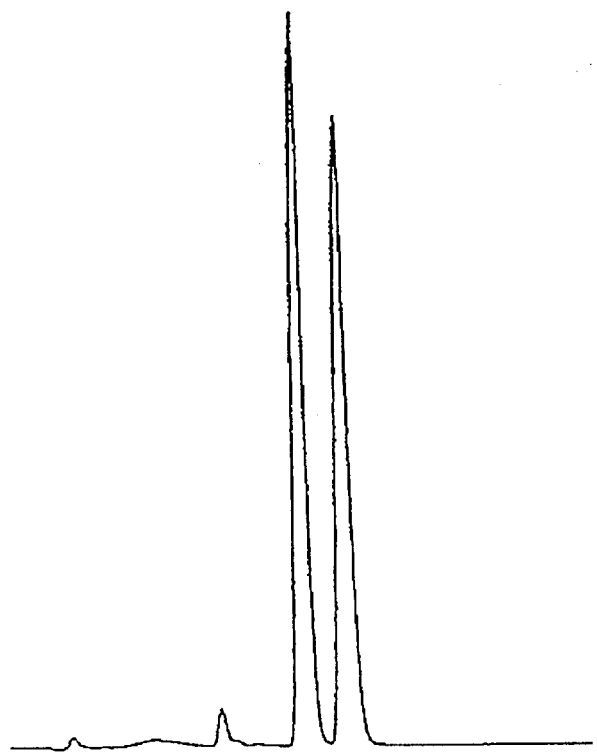
FIG. 20 is a column chromatogram of eperisone as obtained in Example 9.

The optical resolution of eperisone was conducted by using as the mobile phase a mixture comprising a 20 mM aqueous solution (pH 9) of $Na_2B_4O_7/H_3BO_3$ and $CH_3CN$ at a volume ratio of 40:60. The other experimental conditions were the same as in Example 1. The chromatogram thus obtained is shown in FIG. 20, and the retention times and capacity ratios of both enantiomers and the separation factor are given in Table 9.

Comparative Example 12

Figure 21:
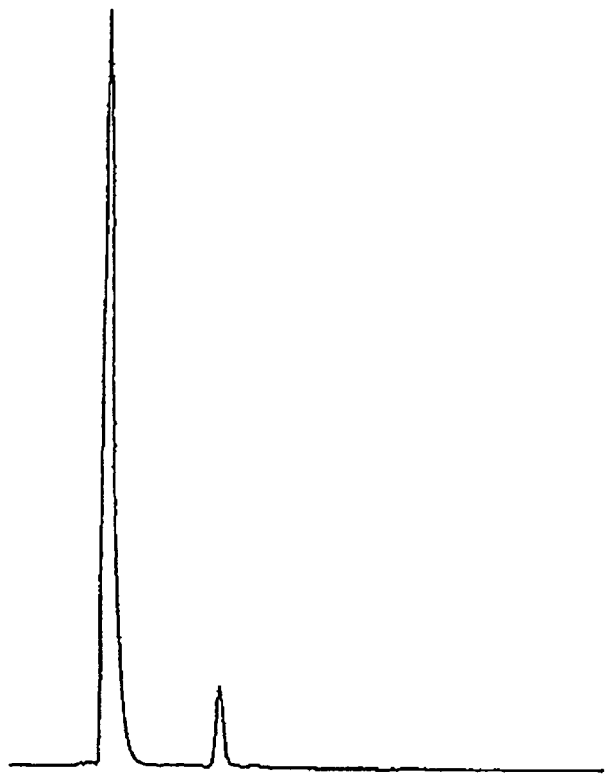
FIG. 21 is another column chromatogram of eperisone as obtained in Comparative Example 12.

The optical resolution of eperisone was conducted by using as the mobile phase a mixed solvent comprising a 0.1 M aqueous solution (pH 4.7) of $KPF_6$ and $CH_3CN$ at a volume ratio of 60:60. The other experimental conditions were the same as in Example 1. The chromatogram thus obtained is shown in FIG. 21, and the retention times and capacity ratios of both enantiomers and the separation factor are given in Table 9. The separation of eperisone into enantiomers failed.

TABLE 9

| | Eperisone | | | | |
|---|---|---|---|---|---|
| | retention time (min.) | | capacity ratio (k') | | separation factor |
| | 1 | 2 | 1 | 2 | (α) |
| Ex. 9 | 15.03 | 17.27 | 3.18 | 3.77 | 1.19 |
| Comp. Ex. 12 | 5.02 | — | 0.39 | — | 1 |

Example 10

Figure 22:
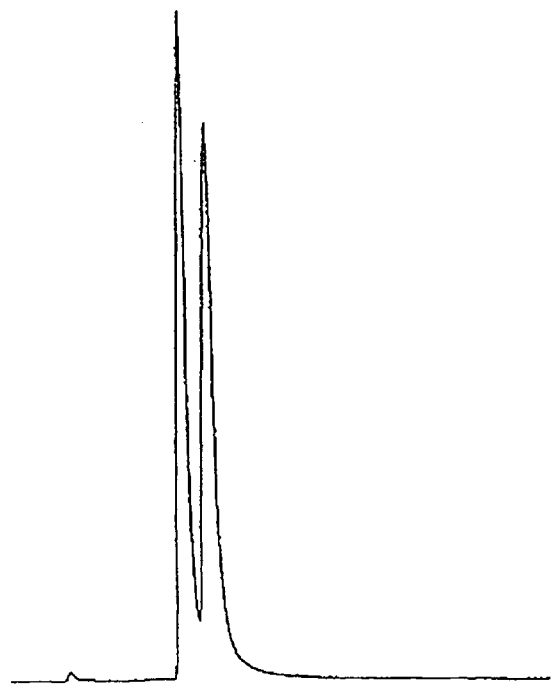
FIG. 22 is a column chromatogram of propafenone as obtained in Example 10.

The optical resolution of propafenone was conducted by using as the mobile phase a mixture comprising a 20 mM aqueous solution (pH 9) of $Na_2B_4O_7/H_3BO_3$ and $CH_3CN$ at a volume ratio of 40:60. The other experimental conditions were the same as in Example 1. The chromatogram thus obtained is shown in FIG. 22, and the retention times and capacity ratios of both enantiomers and the separation factor are given in Table 10.

Comparative Example 13

Figure 23:
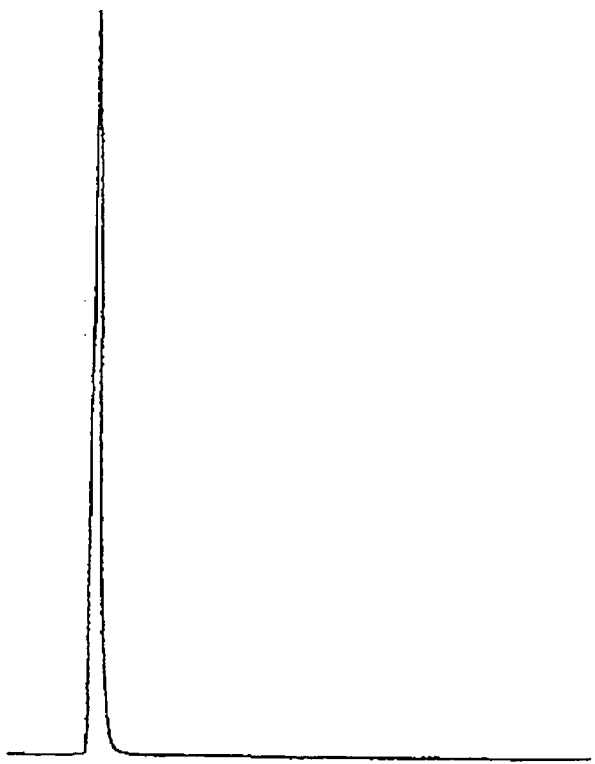
FIG. 23 is another column chromatogram of propafenone as obtained in Comparative Example 13.

The optical resolution of propafenone was conducted by using as the mobile phase a mixed solvent comprising a 0.1 M aqueous solution (pH 4.7) of $KPF_6$ and $CH_3CN$ at a volume ratio of 40:60. The other experimental conditions were the same as in Example 1. The chromatogram thus obtained is shown in FIG. 23, and the retention times and capacity ratios of both enantiomers and the separation factor are given in Table 10. The separation of propafenone into enantiomers failed.

TABLE 10

| | Propafenone | | | | |
|---|---|---|---|---|---|
| | retention time (min.) | | capacity ratio (k') | | separation factor |
| | 1 | 2 | 1 | 2 | (α) |
| Ex. 10 | 9.70 | 11.12 | 1.69 | 2.09 | 1.24 |
| Comp. Ex. 13 | 4.74 | — | 0.32 | — | 1 |

Example 11

Figure 24:
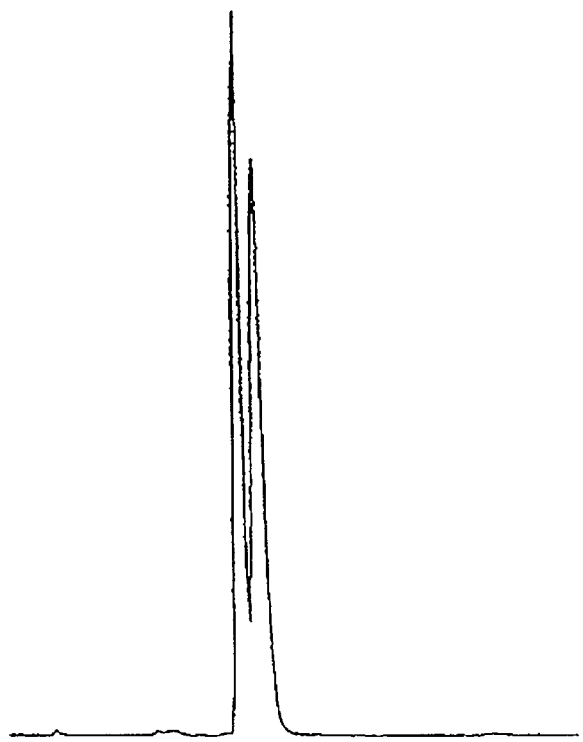
FIG. 24 is a column chromatogram of profenamine as obtained in Example 11.

The optical resolution of profenamine was conducted by using as the mobile phase a mixture comprising a 20 mM aqueous solution (pH 9) of $Na_2B_4O_7/H_3BO_3$ and $CH_3CN$ at a volume ratio of 40:60. The other experimental conditions were the same as in Example 1. The chromatogram thus obtained is shown in FIG. 24, and the retention times and capacity ratios of both enantiomers and the separation factor are given in Table 11.

Comparative Example 14

Figure 25:
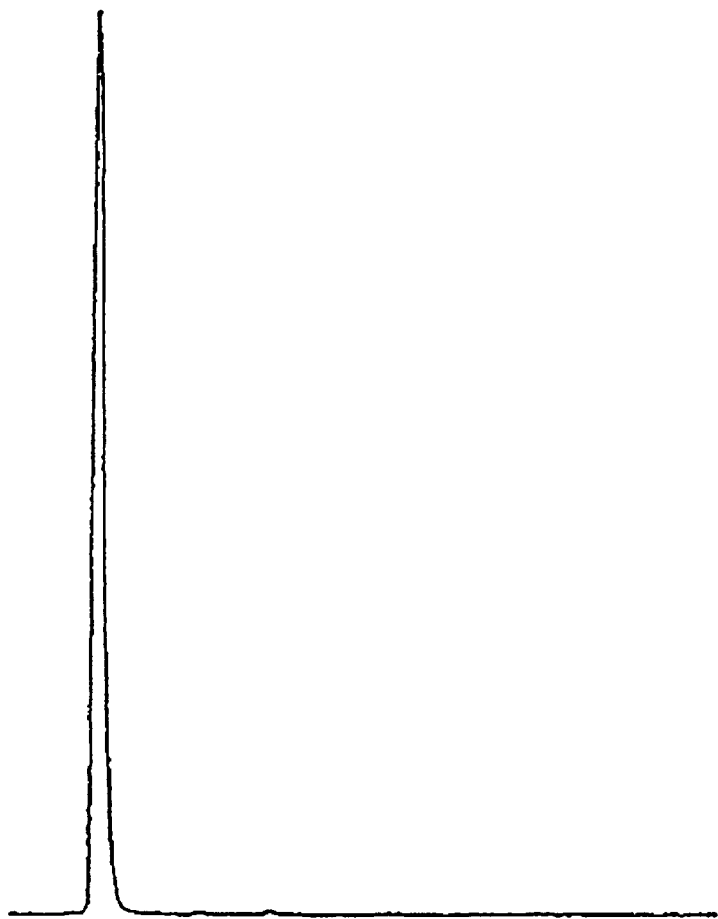
FIG. 25 is another column chromatogram of profenamine as obtained in Comparative Example 14.

The optical resolution of profenamine was conducted by using as the mobile phase a mixed solvent comprising a 0.1 M aqueous solution (pH 4.7) of $KPF_6$ and $CH_3CN$ at a volume ratio of 40:60. The other experimental conditions were the same as in Example 1. The chromatogram thus obtained is shown in FIG. 25, and the retention times and capacity ratios of both enantiomers and the separation factor are given in Table 11. The separation of profenamine into enantiomers failed.

TABLE 11

| | Profenamine | | | | |
|---|---|---|---|---|---|
| | retention time (min.) | | capacity ratio (k') | | separation factor |
| | 1 | 2 | 1 | 2 | (α) |
| Ex. 11 | 16.34 | 17.66 | 3.54 | 3.91 | 1.10 |
| Comp. Ex. 14 | 5.22 | — | 0.45 | — | 1 |

What is claimed is:

1. In a method for separating optical isomers by liquid chromatography with a separating agent, the improvement comprising passing said optical isomers through a polysaccharide derivative as the active component in the reverse phase condition using a basic mobile phase.

2. The method according to claim 1, in which the basic mobile phase is a solution comprising a basic compound and a mixture of water with a water-soluble organic solvent.

3. The method according to claim 2, in which the basic compound is a basic inorganic salt.

4. The method according to claim 2, in which the basic compound is a phosphate.

5. The method according to claim 2, in which the basic compound is $K_2HPO_4$, $Na_3PO_4$ or a mixture thereof.

6. The method according to claim 2, in which the basic compound is a borate.

7. The method according to claim 2, in which the basic compound is $Na_2B_4O_7$ or a mixture thereof with $H_3BO_3$.

8. The method according to claim 1, in which the polysaccharide derivative is a polysaccharide carbamate.

9. The method according to claim 1, in which the polysaccharide derivative is amylose tris(3,5-dimethylphenylcarbamate).

* * * * *